United States Patent [19]

McCall

[11] Patent Number: 4,556,656
[45] Date of Patent: Dec. 3, 1985

[54] 2-BENZOXEPINS

[75] Inventor: John M. McCall, Kalamazoo, Mich.

[73] Assignee: The Upjohn Company, Kalamazoo, Mich.

[21] Appl. No.: 26,718

[22] Filed: Apr. 4, 1979

Related U.S. Application Data

[60] Continuation-in-part of Ser. No. 953,574, Oct. 23, 1978, abandoned, which is a division of Ser. No. 847,350, Oct. 31, 1977, abandoned.

[51] Int. Cl.$^4$ .............. A61K 31/335; A61K 31/445; A61K 31/495; C07D 313/08; C07D 295/02
[52] U.S. Cl. .................... 514/227; 514/255; 514/315; 514/450; 544/147; 544/238; 544/283; 544/295; 544/353; 544/357; 544/360; 544/366; 544/369; 544/371; 544/376; 546/149; 546/196; 546/199; 546/269; 548/525; 549/330; 549/355
[58] Field of Search ............... 260/333; 544/376, 147, 544/238, 283, 295, 353, 357, 360, 366, 369, 371; 424/250; 546/149, 196, 199, 269; 548/525; 549/330, 355; 514/227, 255, 315, 450

[56] References Cited

U.S. PATENT DOCUMENTS

| | | | |
|---|---|---|---|
| 3,467,675 | 9/1969 | Petersen et al. | 260/346.2 |
| 4,066,648 | 1/1978 | Oka et al. | 544/402 |
| 4,153,612 | 5/1979 | McCall | 260/333 |
| 4,166,062 | 8/1979 | McCall et al. | 260/333 |
| 4,179,510 | 12/1979 | McCall | 424/250 |
| 4,181,665 | 1/1980 | McCall | 260/340.5 |
| 4,247,553 | 1/1981 | McCall | 424/250 |
| 4,251,526 | 2/1981 | McCall | 424/248.51 |
| 4,279,904 | 7/1981 | Ohlendorf et al. | 424/246 |
| 4,312,868 | 1/1982 | McCall | 424/249 |
| 4,487,774 | 12/1984 | McCall | 424/256 |

Primary Examiner—Donald G. Daus
Assistant Examiner—Stephen M. Kapner
Attorney, Agent, or Firm—Sidney B. Williams, Jr.; Joan Thierstein

[57] ABSTRACT

Isochromans, isothiochromans, 2-benzoxepins, and 2-benzothiepins are described. The compounds possess hypotensive and anti-psychotic properties; methods and compositions using them are described.

122 Claims, No Drawings

2-BENZOXEPINS

CROSS REFERENCE TO RELATED APPLICATION

This application is a continuation-in-part of application Ser. No. 953,574, filed Oct. 23, 1978 now abandoned which is a divisional of Ser. No. 847,350 filed Oct. 31, 1977, also abandoned.

SUMMARY OF THE INVENTION

The present application relates to novel compounds which are amines of certain 2-benzoxepins. In particular the present invention relates to the novel 2-benzoxepins disclosed in U.S. Ser. No. 858,303, now a U.S. Pat. No. 4,153,612, the disclosure of which is incorporated hereby reference.

DETAILED DESCRIPTION OF THE INVENTION

In particular, U.S. Ser. No. 858,303 now U.S. Pat. No. 4,153,612 describes the use of certain 2-benzoxepins as intermediates for preparing 2-benzoxepin amine type compounds. With respect to the specification of U.S. Ser. No. 858,303, now U.S. Pat. No. 4,153,612 particular reference is made to Examples 1 through 9, 10A through 10i, Example 11 for compounds in Table 8 and Example 18 for compounds in Table 10.

Moreover, the Examples 1 and 10A provide examples of preparation of amines according to formula of Examples 10b through 10i and of Example 11 in Table 8. Furthermore, Examples 13 through 17 provide examples of preparation of amines according to formula of Example 18 in Table 10. Accordingly, these are described:

1-(4-fluorophenyl)-4-[(1,3,4,5-tetrahydro-7,8-dimethoxy-2-benzoxepin-1-yl)methyl]-piperazine in Example 1;

1-[2-[(1,3,4,5-tetrahydro-7,8-dimethoxy-2-benzoxepin-1-yl)]ethyl]-4-(3-chlorophenyl)piperazine in Example 10A;

1-[2-[(1,3,4,5-tetrahydro-7,8-dimethoxy-2-benzoxepin-1-yl)methoxy]ethyl]-4-(2-methoxyphenyl)-piperazine in Example 13;

1-[2-[(1,3,4,5-tetrahydro-7,8-dimethoxy-2-benzoxepin-1-yl)methoxy]ethyl]-4-hydroxy-4-(3-trifluoromethylphenyl)-piperidine in Example 14;

1-[2-[(1,3,4,5-tetrahydro-7,8-dimethoxy-2-benzoxepin-1-yl)methoxy]ethyl]-4-(4-fiuorophenyl)-piperazine in Example 15;

1-[2-[(1,3,4,5-tetrahydro-7,8-dimethoxy-2-benzoxepin-1-yl)methoxy]ethyl]-4-(4-fluorophenyl)piperazine in Example 16; and 1-[2-[(1,3,4,5-tetrahydro-7,8-dimethoxy-2-benzoxepin-1-yl)methoxy]ethyl]-4-(2-pyridyl)-piperazine in Example 17.

As indicated in the text associated with Examples 1 through 9 in U.S. Ser. No. 858,303, now U.S. Pat. No. 4,153,612 the method of preparing amines of 1-methyl substituted 1,3,4,5-tetrahydro-2-benzoxepins is according to the procedure of Example 1 from 1-bromomethylbenzoxepin and $HNR_9R_{10}$. Likewise, certain additional 2-benzoxepin amine type compounds represent novel chemical entities comprising one aspect of the present invention. Moreover, these novel compounds are prepared by following procedures similar to those of Example 1 in U.S. Ser. No. 858,303, now U.S. Pat. No. 4,153,612 but substituting an appropriate $HNR_{21}R_{22}$ for $HNR_9R_{10}$ as follows:

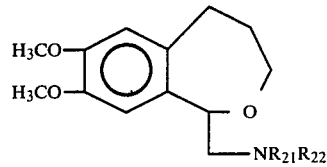

| Example | $NR_{21}R_{22}$ | M.P. (°C.) | Anal. (Found) C | H | N | Cl | Name |
|---|---|---|---|---|---|---|---|
| 9a | —N⟨pyrrolidine⟩ | 224–225°c | 62.57 | 8.31 | 4.06 | 10.95 | 1-[(1,3,4,5-tetrahydro-7,8-dimethoxy-2-benzoxepin-1-yl)methyl]pyrrolidine. |
| 9b | —N(piperazine)N—CH₃ | 225–226°d | 54.60 | 7.61 | 7.05 | 17.98 | 1-methyl-4-[(1,3,4,5-tetrahydro-7,8-dimethoxy-2-benzoxepin-1-yl)methyl]-piperazine. |
| 9c | —N(morpholine)O | 231–232°c | 59.30 | 7.57 | 3.87 | 10.87 | 1-[(1,3,4,5-tetrahydro-7,8-dimethoxy-2-benzoxepin-1-yl)methyl]morpholine. |
| 9d | —N(CH₃)₂ | 188–189°d | | | | | 1-(N,N—dimethylamino)-methyl-1,3,4,5-tetrahydro-7,8-dimethyl-2-benzoxepin. |

-continued

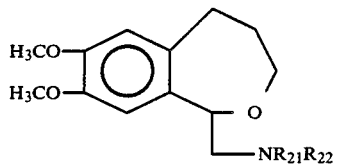

| Example | NR$_{21}$R$_{22}$ | M.P. (°C.) | C | H | N | Cl | Name |
|---|---|---|---|---|---|---|---|
| 9e | —NH-adamantyl | | | | | | 1-(1-adamantylamino)-methyl-1,3,4,5-tetrahydro-7,8-dimethoxy-2-benzoxepin. |
| 9f | —N(n-butyl)H | | | | | | 1-[N—(1-n-butyl)amino]-methyl-1,3,4,5-tetrahydro-7,8-dimethoxy-2-benzoxepin. |
| 9g | —N(n-butyl)$_2$ | | | | | | 1-[N,N—di(1-n-butyl)amino]-methyl-1,3,4,5-tetrahydro-7,8-dimethoxy-2-benzoxepin. |
| 9h | —N(piperidinyl) | 180–183°c | 62.66 | 8.27 | 4.10 | 10.48 | 1-[(1,3,4,5-tetrahydro-7,8-dimethoxy-2-benzoxepin-1-yl)methyl]piperidine. |

Further, in the text associated with Examples 10A through 10i in U.S. Ser. No. 858,303, now U.S. Pat. No. 4,153,612 the method of preparing amines of 1-ethyl substituted-1,3,4,5-tetrahydro-2-benzoxepins is in the manner of Example 10A from 2-[(1,3,4,5-tetrahydro-7,8-dimethoxy-2-benzoxepin-1-yl)]ethyl chloride and HNR$_9$R$_{10}$. Therefore, other 2-benzoxepin amine type compounds represent additional novel chemical compounds comprising the present invention. These compounds are again prepared following procedures nearly the same as those of Example 10A in U.S. Ser. No. 858,303 now U.S. Pat. No. 4,153,612 but substituting an appropriate HNR$_{21}$R$_{22}$ for HNR$_9$R$_{10}$ as follows:

| Example | NR$_{21}$R$_{22}$ | M.P. (°C.) | C | H | N | Cl | Name |
|---|---|---|---|---|---|---|---|
| 10j | —N(piperazinyl)(2-chlorophenyl) | 221–222°c | 61.61 | 7.00 | 6.07 | 15.12 | 1-[2-(1,3,4,5-tetrahydro-7,8-dimethoxy-2-benzoxepin-1-yl)-ethyl]-4-(2-chlorophenyl)piperazine. |
| 10k | —N(4-phenyl-1,2,3,6-tetrahydropyridinyl) | 144.0–144.5 | 76.22 | 8.05 | 3.47 | — | 1-[2-(1,3,4,5-tetrahydro-7,8-dimethoxy-2-benzoxepin-1-yl)ethyl]-4-phenyl-1,2,3,6-tetrahydropyridine. |
| 10l | —N(4-phenylpiperidinyl) | 107.5–108.0 | 75.74 | 8.35 | 3.53 | — | 4-phenyl-1-[2-(1,3,4,5-tetrahydro-7,8-dimethoxy-2-benzoxepin-1-yl)ethyl]-piperidine. |

Furthermore, as disclosed in Example 11 of U.S. Ser. No. 858,303, now U.S. Pat. No. 4,153,612 following the procedure used in Examples 1 through 10 but substituting the appropriate 1-haloalkylbenzoxepin novel compounds similar to those in Table 8 can be made (Table 8a and Table 8b):

TABLE 8a

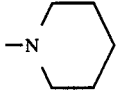

| Example | NR₂₁R₂₂ | M.P. (°C.) | Anal. (Found) C | H | N | Cl | Name |
|---|---|---|---|---|---|---|---|
| 1 | 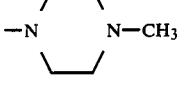 | 248–250°c | | | | | 1-[(1,3,4,5-tetrahydro-7,8-dimethoxy-4,4-dimethyl-2-benzoxepin-1-yl)methyl]piperidine. |
| 2 | 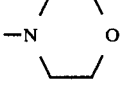 | 239–241°d | | | | | 4-methyl-1-[(1,3,4,5-tetrahydro-7,8-dimethoxy-4,4-dimethyl-2-benzoxepin-1-yl)methyl]piperazine. |
| 3 | —NHButyl | | | | | | 1-[N—(1-n-butyl)amino]-methyl-1,3,4,5-tetrahydro-7,8-dimethoxy-4,4-dimethyl-2-benzoxepin. |
| 4 | 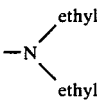 | | | | | | 1-[(1,3,4,5-tetrahydro-7,8-dimethoxy-4,4-dimethyl-2-benzoxepin-1-yl)-methyl]morpholine. |
| 5 | 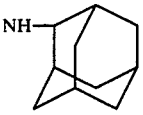 | | | | | | 1-(N,N—diethylamino)-methyl-1,3,4,5-tetrahydro-7,8-dimethoxy-4,4-dimethyl-2-benzoxepin. |
| 6 | 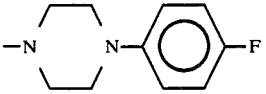 | | | | | | 1-(1-adamantylamino)-methyl-1,3,4,5-tetrahydro-7,8-dimethoxy-4,4-dimethyl-2-benzoxepin. |

TABLE 8b

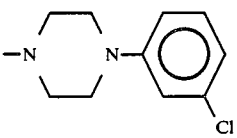

| Example | NR₂₁R₂₂ | M.P. (°C.) | Anal. (Found) C | H | N | Cl | Name |
|---|---|---|---|---|---|---|---|
| 1 | —N(piperazinyl)-C₆H₄-F | 210–212°d | 60.45 | 7.18 | 5.52 | 13.90 | 4-(4-fluorophenyl)-1-[2-(1,3,4,5-tetrahydro-7,8-dimethoxy-4,4-dimethyl-2-benzoxepin-1-yl)ethyl]-piperazine. |
| 2 | —N(piperazinyl)-C₆H₄-Cl | 172–173°d | 58.57 | 7.58 | 5.04 | 19.25 | 4-(3-chlorophenyl)-1-[2-(1,3,4,5-tetrahydro-7,8-dimethoxy-4,4-dimethyl-2-benzoxepin-1-yl)ethyl]-piperazine. |

TABLE 8b-continued

[Structure: 7,8-dimethoxy-4,4-dimethyl-benzoxepin with (CH$_2$)$_2$NR$_{21}$R$_{22}$ substituent]

| Example | NR$_{21}$R$_{22}$ | M.P. (°C.) | C | H | N | Cl | Name |
|---|---|---|---|---|---|---|---|
| 3 | −N(piperazine)N-(2-chlorophenyl) | 186.5–187.5°c | 63.14 | 7.39 | 5.95 | 14.29 | 4-(2-chlorophenyl)-1-[2-(1,3,4,5-tetrahydro-7,8-dimethoxy-4,4-dimethyl-2-benzoxepin-1-yl)ethyl]-piperazine. |
| 4 | −N(piperazine)N-(2-methoxyphenyl) | 176–177°e | 59.72 | 7.57 | 5.17 | 13.01 | 4-(2-methoxyphenyl)-1-[2-(1,3,4,5-tetrahydro-7,8-dimethoxy-4,4-dimethyl-2-benzoxepin-1-yl)ethyl]-piperazine. |
| 5 | −N(piperazine)N-(2-methylphenyl) | 171–173°d | 63.56 | 7.89 | 6.10 | 13.58 | 4-(2-methylphenyl)-1-[2-(1,3,4,5-tetrahydro-7,8-dimethoxy-4,4-dimethyl-2-benzoxepin-1-yl)ethyl]-piperazine. |
| 6 | −N(piperidine)-phenyl | 135.5–136.5°d | 65.70 | 8.23 | 2.59 | 13.65 | 4-phenyl-1-[2-(1,3,4,5-tetrahydro-7,8-dimethoxy-4,4-dimethyl-2-benzoxepin-1-yl)ethyl]piperidine. |
| 7 | −N(piperazine)N-(4-chlorophenyl) | 203–204°d | 58.33 | 7.45 | 4.98 | 19.21 | 4-(4-chlorophenyl)-1-[2-(1,3,4,5-tetrahydro-7,8-dimethoxy-4,4-dimethyl-2-benzoxepin-1-yl)ethyl]-piperazine. | cdihydrochloride monohydrate.

Finally, as disclosed in Example 18 of U.S. Ser. No. 858,303, now U.S. Pat. No. 4,153,612 following the procedure used in Example 12 through 17 but substituting the 1-[2-[(1,3,4,5,-tetrahydro-2-benzoxepin-1-yl)alkoxy]alkyl chlorides or benzene sulfonates and the appropriate amines the following novel compounds comprise an additional aspect of the present invention:

In all of the above tables, the superscripts on the melting points are c-monohydrochloride; d-dihydrochloride; e-dihydrochloride monohydrate; and f-dihydrochloride dihydrate and g-cyclohexylsulfamate.

In accordance with the above disclosure of novel compounds of the present invention it has now been found that in addition to the preferred compounds of TABLE 10a

[Structure: 7,8-dimethoxy-2-benzoxepin with (CH$_2$)(OCH$_2$H$_2$)NR$_{21}$R$_{22}$ substituent]

| Example | NR$_{21}$R$_{22}$ | M.P. (°C.) | C | H | N | Cl | Name |
|---|---|---|---|---|---|---|---|
| 1 | −N(piperazine)N−CH$_3$ | 210–212°f | 51.00 | 7.85 | 6.18 | 16.12 | 1-[2-[(1,3,4,5-tetrahydro-7,8-dimethoxy-2-benzoxepin-1-yl)methoxy]ethyl]-4-methyl-piperazine. |
| 2 | −N(H)(CH$_2$CH$_2$OH) | 118.5–119.5°g | 54.56 | 7.91 | 5.53 | — | 2-[2-[(1,3,4,5-tetrahydro-7,8-dimethoxy-2-benzoxepin-1-yl)methoxy]ethyl]aminoethanol. |

U.S. Ser. No. 858,303, now U.S. Pat. No. 4,153,612 Formula I' additional amine type 2-benzoxepins are preferred. These additional amine type 2-benzoxepins are as disclosed in U.S. Ser. No. 858,303 now U.S. Pat. No. 4,153,612 but substituting for the group denoted (i) in the definition of A so that A is selected from the group consisting of:

(i) —$(CH_2)_n NR_{21}R_{22}$ wherein n is one to five and $R_{21}$ and $R_{22}$ can be the same or different and are selected from the group consisting of H, alkyl of one through four carbons, and together with the N to which they are attached form heterocyclic rings of four to six ring atoms, morpholine, and $NR_9R_{10}$. Also

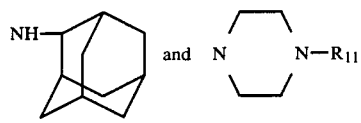

is herein added to the group from which $NR_9R_{10}$ is selected.

Further, the present invention now comprises the unexpected discovery that certain 2-benzoxepin amine type compounds of U.S. Ser. No. 858,303 now U.S. Pat. No. 4,153,162 and the novel compounds of the present invention exhibit a split in activity between an antipsychotic and a hypotensive effect. In other words, such compounds have first, either a high antipsychotic and low cardiovascular effect or second, a low antipsychotic and high cardiovascular effect. For example, the effect of the first split recited above is exhibited by 1-[2-(1,3,4,5-tetrahydro-7,8-dimethoxy-2-benzoxepin-1-yl-ethyl]-4-(2-chlorophenyl)-piperazine. The effect of the second split recited above is exhibited by 1-[2-(1,3,4,5-tetrahydro-7,8-dimethoxy-2-benzoxepin-1-yl)ethyl]-1,2,3,6-tetrahydro-4-(4-chlorophenyl)-pyridine and 1-[2-[(1,3,4,5-tetrahydro-7,8-dimethoxy-2-benzoxepin-1-yl)]ethyl]-4-(2-pyridyl)piperazine which are disclosed as Examples 10f and 10i respectively in U.S. Ser. No. 858,303 now U.S. Pat. No. 4,153,162.

It has now also been discovered that certain 2-benzoxepin amine type compounds of the present invention exhibit antidiabetic effects. These compounds are disclosed herein in Examples 9a through 9h and in Examples 1 through 6 in Table 8a also of the present disclosure.

In the formulation of compounds in the present invention for pharmacological utility conventional techniques are used as fully disclosed in U.S. Ser. No. 858,303 now U.S. Pat. No. 4,153,162.

I claim:

1. Compounds having the formula

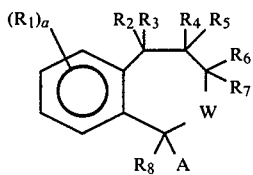

wherein $R_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one $R_1$ is hydroxy, alkoxy or o-methylenedioxy;

a is one through three;

$R_2$ through $R_7$ are the same or different and are selected from the group consisting of hydrogen, alkyl of one through three carbons, inclusive, hydroxy, alkoxy of one through three carbons; phenyl; halo; cycloalkyl of three through six carbons when $R_2$ and $R_3$, $R_4$ and $R_5$, or $R_6$ and $R_7$ are taken together with the carbon to which they are attached; cycloalkyl of four through seven carbons when $R_2$ and $R_4$ or $R_4$ and $R_6$ are taken together with the carbons to which they are attached; and cycloalkyl of five or six carbons, with the over all provisos that no more than one ring may be attached to any one carbon and that at least two of $R_2$ through $R_7$ are hydrogen $R_8$ is alkyl of one through three carbons, hydrogen, or phenyl unsubstituted or substituted with a maximum of three substituents selected from the group consisting of alkyl of one through three carbons, halo, alkoxy of one through three carbons, and trihaloalkyl of one to two carbons;

W is oxygen; and A is selected from the group consisting of:

(i) —$(CH_2)_n NR_{21}R_{22}$, wherein n is one to five and $NR_{21}R_{22}$ is selected from the group consisting of $NR'_{21}R'_{22}$ wherein $R'_{21}$ and $R'_{22}$ can be the same or different and are selected from the group consisting of H, alkyl of one through four carbons, and together with N to which they are attached form heterocyclic rings of four to six ring atoms; morpholino and $NR_9R_{10}$;

(ii) —$(CH_2)_m$—$(OCH_2CH_2)_q$—$NR_{21}R_{22}$, wherein m and q are each one to three, and $NR_{21}R_{22}$ is selected from the group consisting of $NR''_{21}R''_{22}$ wherein $R''_{21}$ and $R''_{22}$ can be the same or different and are selected from the group consisting of H, alkyl of one through four carbons, and together with the N to which they are attached form heterocyclic rings of four to six ring atoms; morpholino; $NHCH_2CH_2OH$ and $NR_9R_{10}$;

(iii) 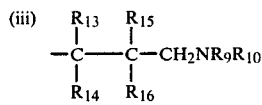

(iv) 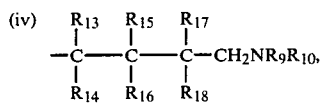

(v) 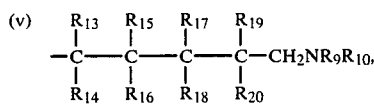

wherein $NR_9R_{10}$ is an amine selected from the group consisting of:

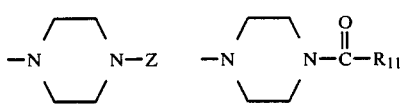

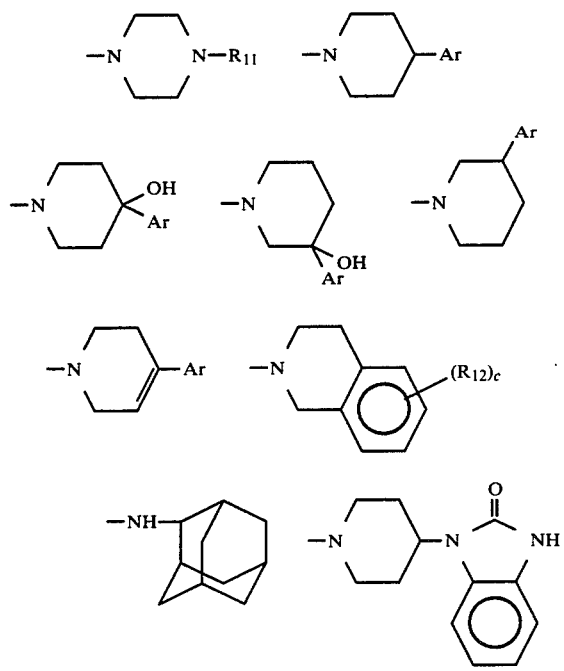

and
—NHCH₂CH₂Ar' wherein $R_{11}$ is alkyl of one through four carbons, 2-furyl, Ar, alkoxy of one to three carbon atoms, inclusive, Z is selected from the group consisting of pyridyl, pyrimidinyl, triazinyl, pyrazinyl, pyridazinyl, pyrrolyl, imidazolyl, pyrazolyl, furyl, tetrazyl, oxazolyl, quinoxalinyl, and quinazolinyl, wherein each member of the group can be unsubstituted or substituted with one or two substituents selected from the group consisting of alkyl of one through three carbons, inclusive, alkoxy of one through three carbons, inclusive, hydroxy, halo, and haloalkyl of one through three carbons, inclusive; provided that Z is not 2-furyl;

$R_{12}$ is alkyl or alkoxy of one through three carbons, hydroxy, halo, or trihalomethyl, $R_{13}$ through $R_{20}$ may be the same or different and are selected from the group hydrogen and alkyl of from 1 to 2 carbon atoms, inclusive; at least one of $R_{13}$ through $R_{20}$ when present being alkyl;

c is zero through two;

Ar and Ar' are phenyl unsubstituted or substituted with one through three substituents selected from the group consisting of alkyl or alkoxy of one through three carbons, hydroxy, halo, and trihaloalkyl or trihaloalkoxy of one or two carbons and pharmaceutically acceptable acid addition salts thereof.

2. A compound of claim 1 wherein a is two or three.

3. Compounds of claim 2 where A is the group —(CH₂)ₙNR₂₁R₂₂.

4. Compounds of claim 3 wherein W is oxygen, $R_2$ through $R_7$ are the same or different and are selected from the group consisting of hydrogen, alkyl of one through three carbon atoms, inclusive and cycloalkyl of four through seven carbon atoms, inclusive, when $R_2$ and $R_4$ or $R_4$ and $R_6$ are taken together with the carbon atom to which they are attached.

5. Compounds of claim 4 wherein $(R_1)_a$ is 7,8-dimethoxy, $R_2$ through $R_7$ are hydrogen and n is one.

6. A compound according to claim 5 wherein $NR_{21}R_{22}$ is 4-(2-methoxyphenyl)-piperazinyl so that the specific embodiment is 1-(2-methoxyphenyl)-4-[(1,3,4,5-tetrahydro-7,8-dimethoxy-2-benzoxepin-1-yl)methyl]-piperazine.

7. The monohydrochloride, hemihydrate of the compound of claim 6.

8. A compound according to claim 5 wherein $NR_{21}R_{22}$ is 4-(4-fluorophenyl)-piperazinyl so that the specific embodiment 1-(4-fluorophenyl)-4-[(1,3,4,5-tetrahydro-7,8-dimethoxy-2-benzoxepin-1-yl)methyl]piperazine.

9. A compound according to claim 5 wherein $NR_{21}R_{22}$ is 4-phenylpiperazinyl so that the specific embodiment is 1-(4-phenyl)-4-[(1,3,4,5-tetrahydro-7,8-dimethoxy-2-benzoxepin-1-yl)methyl]piperazine.

10. A compound according to claim 5 wherein $NR_{21}R_{22}$ is N-1-methanmine so that the specific embodiment is N-[2-(3,4-dimethoxyphenyl)ethyl]-1,3,4,5-tetrahydro-7,8-dimethoxy-2-benzoxepine-1-methaneamine.

11. The monohydrochloride monohydrate of the compound of claim 10.

12. A compound according to claim 5 wherein $NR_{21}R_{22}$ is 1,2,3,4-tetrahydro-6,7-dimethoxy-2-isoquinoline so that the specific embodiment is 1,2,3,4-tetrahydro-6,7-dimethoxy-2-[(1,3,4,5-tetrahydro-7,8-dimethoxy-2-benzoxepin-1-yl)-methyl]isoquinoline.

13. The monohydrochloride hemihydrate of the compound of claim 12.

14. A compound according to claim 5 wherein $NR_{21}R_{22}$ is 4-(4-methoxyphenyl)-piperazinyl so that the specific embodiment is 1-(4-methoxyphenyl)-4-[(1,3,4,5-tetrahydro-7,8-dimethoxy-2-benzoxepin-1-yl)methyl]-piperazine.

15. The monohydrochloride monohydrate of the compound of claim 14.

16. A compound according to claim 5 wherein $NR_{21}R_{22}$ is 4-(3-trifluoromethylphenyl)-4-hydroxypiperidine so that the specific embodiment is 1[(1,3,4,5-tetrahydro-7,8-dimethoxy-2-benzoexpin-1-yl)methyl]-4-[3-(trifluoromethyl)-phenyl]-4-piperidinol.

17. The monohydrobromide salt of the compound of claim 16.

18. A compound according to claim 5 wherein $NR_{21}R_{22}$ is 4-(2-methylphenyl)-piperazine so that the specific embodiment is 1-(2-methylphenyl)-4-[(1,3,4,5-tetrahydro-7,8-dimethoxy-2-benzoxepin-1-yl)methyl]-piperazine.

19. A compound according to claim 5 wherein $NR_{21}R_{22}$ is 4-(2-pyridinyl)-piperazine so that the specific embodiment is 1-(2-pyridinyl)-4-[(1,3,4,5-tetrahydro-7,8-dimethoxy-2-benzoxepin-1-yl)methyl]piperazine.

20. The monochloride hemihydrate of the compound of claim 19.

21. A compound according to claim 5 wherein $NR_{21}R_{22}$ is pyrrolidinyl so that the specific embodiment is 1-[(1,3,4,5-tetrahydro-7,8-dimethoxy-2-benzoxepin-1-yl)methyl]-pyrrolidine.

22. The monohydrochloride of the compound of claim 21.

23. A compound of claim 5 wherein $NR_{21}R_{22}$ is 4-methylpiperazinyl so that the specific embodiment is 1-methyl-4-[(1,3,4,5-tetrahydro-7,8-dimethoxy-2-benzoxepin-1-yl-methyl]-piperazine.

24. The dihydrochloride of the compound of claim 23.

25. A compound of claim 5 wherein $NR_{21}R_{22}$ is morpholinyl so that the specific embodiment is 1-[(1,3,4,5-tetrahydro-7,8-dimethoxy-2-benzoxepin-1-yl)methyl]-morpholine.

26. The monohydrochloride of the compound of claim 25.

27. A compound of claim 5 wherein $NR_{21}R_{22}$ is N,N-dimethylamino so that the specific embodiment is 1-(N,N-dimethylamino)methyl-1,3,4,5-tetrahydro-7,8-dimethoxy-2-benzoxepin.

28. The monohydrochloride of the compound of claim 27.

29. A compound of claim 5 wherein $NR_{21}R_{22}$ is 1-adamantylamino so that the specific embodiment is 1-(1-adamantylamino)methyl-1,3,4,5-tetrahydro-7,8-dimethoxy-2-benzoxepin.

30. A compound of claim 5 wherein $NR_{21}R_{22}$ is n-butylamino so that the specific embodiment is 1-[N-(1-n-butyl)-amino]methyl-1,3,4,5-tetrahydro-7,8-dimethoxy-2-benzoxepin.

31. A compound of claim 5 wherein $NR_{21}R_{22}$ is N,N-di(1-n-butyl)amino so that the specific embodiment is 1-[N,N-di(1-n-butyl)amino]methyl-1,3,4,5-tetrahydro-7,8-dimethoxy-2-benzoxepin.

32. A compound of claim 5 wherein $NR_{21}R_{22}$ is piperidinyl so that the specific embodiment is 1-[(1,3,4,5-tetrahydro-7,8-dimethoxy-2-benzoxepin-1-yl)methyl]piperidine.

33. The monohydrochloride of the compound of claim 32.

34. Compounds of claim 4 wherein $(R_1)_a$ is 7,8-dimethoxy, $R_2$ through $R_7$ are hydrogen and n is 2.

35. A compound of claim 34 wherein $NR_{21}R_{22}$ is 4-(2-methoxyphenyl)-piperazinyl so that the specific embodiment is 1-[2-(1,3,4,5-tetrahydro-7,8-dimethoxy-2-benzoxepin-1-yl)-ethyl]-4-(2-methoxyphenyl)piperazine.

36. The monohydrochloride hemihydrate of the compound of claim 35.

37. A compound of claim 34 wherein $NR_{21}R_{22}$ is 4-(2-chlorophenyl)piperazinyl so that the specific embodiment is 1-[2-(1,3,4,5-tetrahydro-7,8-dimethoxy-2-benzoxepin-1-yl)-ethyl]-4-(2-chlorophenyl)piperazine.

38. The monohydrochloride of the compound of claim 37.

39. A compound of claim 34 wherein $NR_{21}R_{22}$ is 4-phenyl-1,2,3,6-tetrahydropyridinyl so that the specific embodiment is 1-[2-(1,3,4,5-tetrahydro-7,8-dimethoxy-2-benzoxepin-1-yl)ethyl]-4-phenyl-1,2,3,6-tetrahydropyridine.

40. A compound of claim 34 wherein $NR_{21}R_{22}$ is 4-phenylpiperidinyl so that the specific embodiment is 4-phenyl-1-[2-(1,3,4,5-tetrahydro-7,8-dimethoxy-2-benzoxepin-1-yl)-ethyl]piperidine.

41. A compound of claim 34 wherein $NR_{21}R_{22}$ is 4-(3-chlorophenyl)piperazinyl so that the specific embodiment 1-[2-[(1,3,4,5-tetrahydro-7,8-dimethoxy-2-benzoxepin-1-yl)]ethyl]-4-(3-chlorophenyl)piperazine.

42. A compound of claim 34 wherein $NR_{21}R_{22}$ is 4-(4-fluorophenyl)piperazinyl so that the specific embodiment is 1-[2-(1,3,4,5-tetrahydro-7,8-dimethoxy-2-benzoxepin-1-yl)ethyl]-4-(4-fluorophenyl)piperazine.

43. A compound of claim 34 wherein $NR_{21}R_{22}$ is N-2-[(3,4,-dimethoxyphenyl)ethyl]amino so that the specific embodiment is N-[2-(1,3,4,5-tetrahydro-7,8-dimethoxy-2-benzoxepin-1-yl)ethyl]-N-[2-(3,4-dimethoxyphenyl)ethyl]amine.

44. The monohydrochloride monohydrate of the compound of claim 43.

45. A compound of claim 34 wherein $NR_{21}R_{22}$ is 4-chloropiperazinyl so that the specific embodiment is 1-[2-(1,3,4,5-tetrahydro-7,8-dimethoxy-2-benzoxepin-1-yl)ethyl]-4-(4-chlorophenyl)piperazine.

46. A compound of claim 34 wherein $NR_{21}R_{22}$ is 4-(2-methoxyphenyl)piperazinyl so that the specific embodiment is 1-[2-(1,3,4,5-tetrahydro-7,8-dimethoxy-2-benzoxepin-1-yl)ethyl]-4-(2-methoxyphenyl)piperazine.

47. A compound of claim 34 wherein $NR_{21}R_{22}$ is 4-(2,3-dihydro-2-oxo-1H-benimidazol-1-yl)-piperadinyl so that the specific embodiment is 1-[2-(1,3,4,5-tetrahydro-7,8-dimethoxy-2-benzoxepin-1-yl)ethyl]-4-(2,3-dihydro-2-oxo-1H-benzimidazol-1-yl)piperidine.

48. A compound of claim 34 wherein $NR_{21}R_{22}$ is 4-(2-pyridyl)piperazinyl so that the specific embodiment is 1-[2-[(1,3,4,5-tetrahydro-7,8-dimethoxy-2-benzoxepin-1-yl)]ethyl]-4-(2-pyridyl)piperazine.

49. A compound of claim 34 wherein $NR_{21}R_{22}$ is 4-(4-chlorophenyl)-1,2,3,6-tetrahydropyridinyl so that the specific embodiment is 4-(4-chlorophenyl)-1,2,3,6-tetrahydro-1-[2-(1,3,4,5-tetrahydro-7,8-dimethoxy-2-benzoxepin-1-yl)ethyl]pyridine.

50. Compounds of claim 4 wherein $(R_1)_a$ is 7,8-dimethoxy, $R_2-R_3$ and $R_6-R_7$ are hydrogen, $R_4$ and $R_5$ are methyl and n is one.

51. A compound of claim 50 wherein $NR_{21}R_{22}$ is piperidinyl so that the specific embodiment is 1-[(1,3,4,5-tetrahydro-7,8-dimethoxy-4,4-dimethyl-2-benzoxepin-1-yl)-methyl]piperidine.

52. The monohydrochloride of the compound of claim 51.

53. A compound of claim 50 wherein $NR_{21}R_{22}$ is 4-methylpiperazinyl so that the specific embodiment is 4-methyl-1-[(1,3,4,5-tetrahydro-7,8-dimethoxy-4,4-dimethyl-2-benzoxepin-1-yl)methyl]piperazine.

54. The dihydrochloride of the compound of claim 53.

55. A compound of claim 50 wherein $NR_{21}R_{22}$ is n-butylamino so that the specific embodiment is 1-[N-(1-n-butyl)amino]methyl-1,3,4,5-tetrahydro-7,8-dimethoxy-4,4-dimethyl-2-benzoxepin.

56. A compound of claim 50 wherein $NR_{21}R_{22}$ is morpholinyl so that the specific embodiment is 1-[(1,3,4,5-tetrahydro-7,8-dimethoxy-4,4-dimethyl-2-benzoxepin-1-yl)methyl]morpholine.

57. A compound of claim 50 wherein $NR_{21}R_{22}$ is N,N-diethylamino so that the specific embodiment is 1-(N,N-diethylamino)methyl-1,3,4,5-tetrahydro-7,8-dimethoxy-4,4-dimethyl-2-benzoxepin.

58. A compound of claim 50 wherein $NR_{21}R_{22}$ is 1-adamantylamino so that the specific embodiment is 1-(1-adamantylamino)methyl-1,3,4,5-tetrahydro-7,8-dimethoxy-4,4-dimethyl-2-benzoxepin.

59. Compounds of claim 4 wherein $(R_1)_a$ is 7,8-dimethoxy, $R_2-R_3$ and $R_6-R_7$ are hydrogen, $R_4$ and $R_5$ are methyl and n is two.

60. A compound of claim 59 wherein $NR_{21}R_{22}$ is 4-(4-fluorophenyl)piperazinyl so that the specific embodiment is 4-(4-fluorophenyl)-1-[2-(1,3,4,5-tetrahydro-7,8-dimethoxy-4,4-dimethyl-2-benzoxepin-1-yl)ethyl]-piperazine.

61. The dihydrochloride of the compound of claim 60.

62. A compound of claim 59 wherein NR$_{21}$R$_{22}$ is 4-(3-chlorophenyl)piperazinyl so that the specific embodiment is 4-(3-chlorophenyl)-1-[2-(1,3,4,5-tetrahydro-7,8-dimethoxy-4,4-dimethyl-2-benzoxepin-1-yl)ethyl]-piperazine.

63. The dihydrochloride of the compound of claim 62.

64. A compound of claim 59 wherein NR$_{21}$R$_{22}$ is 4-(2-chlorophenyl)piperazinyl so that the specific embodiment is 4-(2-chlorophenyl)-1-[2-(1,3,4,5-tetrahydro-7,8-dimethoxy-4,4-dimethyl-2-benzoxepin-1-yl)ethyl]-piperazine.

65. The monohydrochloride of the compound of claim 64.

66. A compound of claim 59 wherein NR$_{21}$R$_{22}$ is 4-(2-methoxyphenyl)piperazinyl so that the specific embodiment is 4-(2-methoxyphenyl)-1-[2-(1,3,4,5-tetrahydro-7,8-dimethoxy-4,4-dimethyl-2-benzoxepin-1-yl)ethyl]piperazine.

67. The dihydrochloride monohydrate of the compound of claim 66.

68. A compound of claim 59 wherein NR$_{21}$R$_{22}$ is 4-(2-methylphenyl)piperazinyl so that the specific embodiment is 4-(2-methylphenyl)-1-[2-(1,3,4,5-tetrahydro-7,8-dimethoxy-4,4-dimethyl-2-benzoxepin-1-yl)ethyl]piperazine.

69. The dihydrochloride of the compound of claim 68.

70. A compound of claim 59 wherein NR$_{21}$R$_{22}$ is 4-phenylpiperidinyl so that the specific embodiment is 4-phenyl-1-[2-(1,3,4,5-tetrahydro-7,8-dimethoxy-4,4-dimethyl-2-benzoxepin-1-yl)ethyl]piperidine.

71. The dihydrochloride of the compound of claim 70.

72. A compound of claim 59 wherein NR$_{21}$R$_{22}$ is 4-(4-chlorophenyl)piperazinyl so that the specific embodiment is 4-(4-chlorophenyl)-1-[2-(1,3,4,5-tetrahydro-7,8-dimethoxy-4,4-dimethyl-2-benzoxepin-1-yl)ethyl]-piperazine.

73. The dihydrochloride of the compound of claim 72.

74. Compounds of claim 1 wherein W is oxygen and A is selected from the group consisting of —(CH$_2$)-$_m$(OCH$_2$CH$_2$)$_q$—NR$_{21}$R$_{22}$.

75. Compounds of claim 74 wherein R$_2$ through R$_7$ are the same or different and are selected from the group consisting of hydrogen, alkyl of one to three carbon atoms, inclusive, and cycloalkyl of four through seven carbon atoms, inclusive, when R$_2$ and R$_4$ are taken together with the carbon atom to which they are attached.

76. Compounds of claim 75 wherein (R$_1$)$_a$ is 7,8-dimethoxy, R$_2$ through R$_7$ are hydrogen and A is —CH$_2$OCH$_2$CH$_2$NR$_{21}$R$_{22}$.

77. A compound of claim 76 wherein NR$_{21}$R$_{22}$ is 4-[3-(trifluoromethyl)phenyl]-4-piperidinol so that the specific embodiment is 1-[2-[(1,3,4,5-tetrahydro-7,8-dimethoxy-2-benzoxepin-1-yl)methoxy]ethyl]-4-[3-(trifluoromethyl)-phenyl]-4-piperidinol.

78. The monohydrochloride hemihydrate salt of the compound of claim 77.

79. A compound of claim 76 wherein NR$_{21}$R$_{22}$ is 4-(2-methoxyphenyl)piperazinyl so that the specific embodiment is 1-(2-methoxyphenyl)-4-[2-[(1,3,4,5-tetrahydro-7,8-dimethoxy-2-benzoxepin-1-yl)methoxy]ethyl]piperazine.

80. The dihydrochloride monohydrate salt of the compound of claim 79.

81. A compound of claim 76 wherein NR$_{21}$R$_{22}$ is 4-(2-pyridyl)piperazinyl so that the specific embodiment is 1-(2-pyridyl)-4-[2-[(1,3,4,5-tetrahydro-7,8-dimethoxy-2-benzoxepin-1-yl)methoxy]ethyl]piperazine.

82. The hydrochloride salt of the compound of claim 81.

83. A compound of claim 76 wherein NR$_{21}$R$_{22}$ is 4-(4-fluorophenyl)-piperazinyl so that the specific embodiment is 1-(4-fluorophenyl)-4-2-[(1,3,4,5-tetrahydro-7,8-dimethoxy-2-benzoxepin-1-yl)methoxy]ethyl]-piperazine.

84. The dihydrochloride salt of the compound of claim 83.

85. A compound of claim 76 wherein A is —CH$_2$—O—CH$_2$CH$_2$—NR$_{21}$R$_{22}$ and NR$_{21}$R$_{22}$ is 4-methylpiperazinyl so that the specific embodiment is 1-[2-[(1,3,4,5-tetrahydro-7,8-dimethoxy-2-benzoxepin-1-yl)methoxy]-ethyl]-4-methylpiperazine.

86. The dihydrochloride dihydrate of the compound of claim 85.

87. A compound of claim 76 wherein A is —CH$_2$—O—CH$_2$CH$_2$—NR$_{21}$R$_{22}$ and NR$_{21}$R$_{22}$ is amino ethanol so that the specific embodiment is 2-[2-[(1,3,4,5-tetrahydro-7,8-dimethoxy-2-benzoxepin-1-yl)methoxy]ethyl]aminoethanol.

88. The cyclohexyl sulfamate of the compound of claim 87.

89. A pharmaceutical composition comprising a dosage unit form having 0.5 to 300 mg of a compound selected from the group consisting of compounds having the formula:

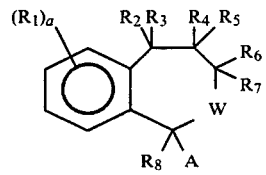

wherein

R$_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one R$_1$ is hydroxy, alkoxy or o-methylenedioxy;

a is one through three;

R$_2$ through R$_7$ are the same or different and are selected from the group consisting of hydrogen, alkyl of one through three carbons, inclusive, hydroxy, alkoxy of one through three carbons; phenyl; halo; cycloalkyl of three through six carbons when R$_2$ and R$_3$, R$_4$ and R$_5$, or R$_6$ and R$_7$ are taken together with the carbon to which they are attached; cycloalkyl of four through seven carbons when R$_2$ and R$_4$ or R$_4$ and R$_6$ are taken together with the carbons to which they are attached; and cycloalkyl of five or six carbons, with the overall provisos that no more than one ring may be attached to any one carbon and that at least two of R$_2$ through R$_7$ are hydrogen.

R$_8$ is alkyl of one through three carbons, hydrogen, or phenyl unsubstituted or substituted with a maximum of three substituents selected from the group consisting of alkyl of one through three carbons, halo, alkoxy of one through three carbons, and trihaloalkyl of one to two carbons;

W is oxygen;

and A is selected from the group consisting of:

(i) —(CH$_2$)$_n$NR$_{21}$R$_{22}$, wherein n is one to five and NR$_{21}$R$_{22}$ is selected from the group consisting of NR'$_{21}$R'$_{22}$ wherein R'$_{21}$ and R'$_{22}$ can be the same or different and are selected from the group consisting of H, alkyl of one through four carbons, and together with N to which they are attached from heterocyclic rings of four to six ring atoms; morpholino and NR$_9$R$_{10}$;

(ii) —(CH$_2$)$_m$—(OCH$_2$CH$_2$)$_q$—NR$_{21}$R$_{22}$, wherein m and q are each one to three, and NR$_{21}$R$_{22}$ is selected from the group consisting of NR''$_{21}$R''$_{22}$ wherein R''$_{21}$ and R''$_{22}$ can be the same or different and are selected from the group consisting of H, alkyl of one through four carbons, and together with the N to which they are attached form heterocyclic rings of four to six ring atoms; morpholino; NHCH$_2$CH$_2$OH and NR$_9$R$_{10}$;

(iii) 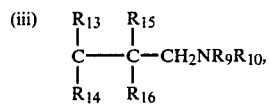

(iv) 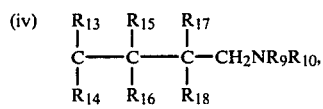

(v) 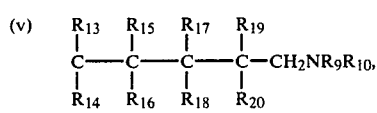

wherein NR$_9$R$_{10}$ is an amine selected from the group consisting of:

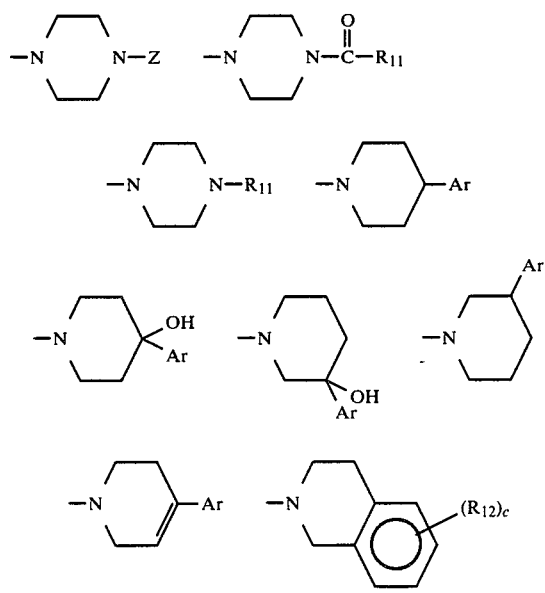

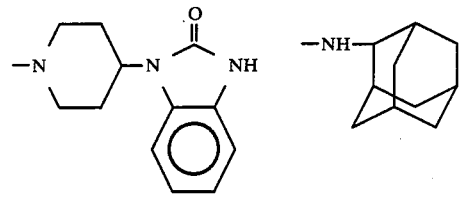

and

—NHCH$_2$CH$_2$Ar' wherein R$_{11}$ is alkyl of one through four carbons, 2-furyl, Ar, alkoxy of one to three carbon atoms, inclusive, Z is selected from the group consisting of pyridyl, pyrimidinyl, triazinyl, pyrazinyl, pyridazinyl, pyrrolyl, imidazolyl, pyrazolyl, furyl, tetrazyl, oxazolyl, quinoxalinyl, and quinazolinyl, wherein each member of the group can be unsubstituted or substituted with one or two substituents selected from the group consisting of alkyl of one through three carbons, inclusive, alkoxy of one through three carbons, inclusive, hydroxy, halo, and haloalkyl of one through three carbons, inclusive; provided that Z is not 2-furyl;

R$_{12}$ is alkyl or alkoxy of one through three carbons, hydroxy, halo, or trihalomethyl, R$_{13}$ through R$_{20}$ may be the same or different and are selected from the group hydrogen and alkyl of from 1 to 2 carbon atoms, inclusive; at least one of R$_{13}$ through R$_{20}$ when present being alkyl;

c is zero through two;

Ar and Ar' are phenyl unsubstituted or substituted with one through three substituents selected from the group consisting of alkyl or alkoxy of one through three carbons, hydroxy, halo, and trihaloalkyl or trihaloalkoxy of one or two carbons and pharmaceutically acceptable acid addition salts thereof.

90. A pharmaceutical composition of claim 89 wherein a is two or three.

91. Compositions of claim 90 when A is the group —(CH$_2$)$_n$NR$_{21}$R$_{22}$.

92. Compositions of claim 91 wherein W is oxygen, R$_2$ through R$_7$ are the same or different and are selected from the group consisting of hydrogen, alkyl of one through three carbon atoms, inclusive and cycloalkyl of four through seven carbon atoms, inclusive, when R$_2$ and R$_4$ or R$_4$ and R$_6$ are taken together with the carbon atom to which they are attached.

93. A composition according to claim 92 wherein (R$_1$)$_a$ is 7,8-dimethoxy, R$_2$ through R$_7$ are hydrogen and n is one.

94. A composition according to claim 93 wherein the therapeutically effective compound is selected from the group consisting of:

1-(2-methoxyphenyl)-4-[(1,3,4,5-tetrahydro-7,8-dimethoxy-2-benzoxepin-1-yl)methyl]piperazine, 1-(2-methoxyphenyl)-4-[(1,3,4,5-tetrahydro-7,8-dimethoxy-2-benzoxepin-1-yl)methyl]piperazine monohydrochloride, hemihydrate, 1-(4-fluorophenyl)-4-[(1,3,4,5-tetrahydro-7,8-dimethoxy-2-benzoxepin-1-yl)methyl]piperazine, 1-(4-phenyl)-4-[(1,3,4,5-tetrahydro-7,8-dimethoxy-2-benzoxepin-1-yl)methyl]piperazine, N-[2-(3,4-dimethoxyphenyl)ethyl]-1,3,4,5-tetrahydro-7,8-dimethoxy-2-benzoxepine-1-methaneamine,
N-[2-(3,4-dimethoxyphenyl)ethyl]-1,3,4,5-tetrahydro-7,8-dimethoxy-2-benzoxepine-1-methaneamine monohydrochloride monohydrate,
1,2,3,4-tetrahydro-6,7-dimethoxy-2-[(1,3,4,5-tetrahydro-7,8-dimethoxy-2-benzoxepin-1-yl)methyl]isoquinoline,
1,2,3,4-tetrahydro-6,7-dimethoxy-2-[(1,3,4,5-tetrahydro-7,8-dimethoxy-2-benzoxepin-1-yl)methyl]isoquinoline monohydrochloride hemihydrate,
1-(4-methoxyphenyl)-4-[(1,3,4,5-tetrahydro-7,8-dimethoxy-2-benzoxepin-1-yl)methyl]piperazine,
1-(4-methoxyphenyl)-4-[(1,3,4,5-tetrahydro-7,8-dimethoxy-2-benzoxepin-1-yl)methyl]piperazine monohydrochloride monohydrate,
1[(1,3,4,5-tetrahydro-7,8-dimethoxy-2-benzoxepin-1-yl)methyl]-4-[3-(trifluoromethyl)phenyl]-4-piperidinol,
1[(1,3,4,5-tetrahydro-7,8-dimethoxy-2-benzoxepin-1-yl)methyl]-4-[3-(trifluoromethyl)phenyl]-4-piperidinol monohydrobromide,
1-(2-methylphenyl)-4-[(1,3,4,5-tetrahydro-7,8-dimethoxy-2-benzoxepin-1-yl)methyl]piperazine,
1-(2-pyridinyl)-4-[(1,3,4,5-tetrahydro-7,8-dimethoxy-2-benzoxepin-1-yl)methyl]piperazine,
1-(2-pyridinyl)-4-[(1,3,4,5-tetrahydro-7,8-dimethoxy-2-benzoxepin-1-yl)methyl]piperazine monohydrochloride hemihydrate,
1-[(1,3,4,5-tetrahydro-7,8-dimethoxy-2-benzoxepin-1-yl)methyl]pyrrolidine,
1-[(1,3,4,5-tetrahydro-7,8-dimethoxy-2-benzoxepin-1-yl)methyl]pyrrolidine monohydrochloride,
1-methyl-4[(1,3,4,5-tetrahydro-7,8-dimethoxy-2-benzoxepin-1-yl)methyl]piperazine,
1-methyl-4[(1,3,4,5-tetrahydro-7,8-dimethoxy-2-benzoxepin-1-yl)methyl]piperazine dihydrochloride,
1-[(1,3,4,5-tetrahydro-7,8-dimethoxy-2-benzoxepin-1-yl)methyl]morpholine,
1-[(1,3,4,5-tetrahydro-7,8-dimethoxy-2-benzoxepin-1-yl)methyl]morpholine monohydrochloride,
1-(N,N-dimethylamino)methyl-1,3,4,5-tetrahydro-7,8-dimethoxy-2-benzoxepin,
1-(N,N-dimethylamino)methyl-1,3,4,5-tetrahydro-7,8-dimethoxy-2-benzoxepin monohydrochloride,
1-(1-adamantylamino)methyl-1,3,4,5-tetrahydro-7,8-dimethoxy-2-benzoxepin,
1-[N-(1-n-butyl)amino]methyl-1,3,4,5-tetrahydro-7,8-dimethoxy-2-benzoxepin,
1-N,N-di(1-n-butyl)amino]methyl-1,3,4,5-tetrahydro-7,8-dimethoxy-2-benzoxepin,
1-[(1,3,4,5-tetrahydro-7,8-dimethoxy-2-benzoxepin-1-yl)methyl]piperidine,
1-[(1,3,4,5-tetrahydro-7,8-dimethoxy-2-benzoxepin-1-yl)methyl]piperidine hydrochloride.

95. A composition according to claim 92 wherein $(R_1)_a$ is 7,8-dimethoxy, $R_2$ through $R_7$ are hydrogen and n is 2.

96. A composition according to claim 95 wherein the therapeutically effective compound is selected from the group consisting of:
1-[2-(1,3,4,5-tetrahydro-7,8-dimethoxy-2-benzoxepin-1-yl)-ethyl]-4-(2-methoxyphenyl)piperazine,
1-[2-(1,3,4,5-tetrahydro-7,8-dimethoxy-2-benzoxepin-1-yl)-ethyl]-4-(2-methoxyphenyl)piperazine monohydrochloride hemihydrate,
1-[2-(1,3,4,5-tetrahydro-7,8-dimethoxy-2-benzoxepin-1-yl)-ethyl]-4-(2-chlorophenyl)piperazine,
1-[2-(1,3,4,5-tetrahydro-7,8-dimethoxy-2-benzoxepin-1-yl)-ethyl]-4-(2-chlorophenyl)piperazine monohydrochloride,
1-[2-(1,3,4,5-tetrahydro-7,8-dimethoxy-2-benzoxepin-1-yl)ethyl]-4-phenyl-1,2,3,6-tetrahydropyridine,
4-phenyl-1-[2-(1,3,4,5-tetrahydro-7,8-dimethoxy-2-benzoxepin-1-yl)ethyl]piperidine,
1-[2-[(1,3,4,5-tetrahydro-7,8-dimethoxy-2-benzoxepin-1-yl)]ethyl]-4-(3-chlorophenyl)piperazine,
1-[2-[(1,3,4,5-tetrahydro-7,8-dimethoxy-2-benzoxepin-1-yl)]ethyl]-4-(4-fluorophenyl)piperazine,
N-[2-(1,3,4,5-tetrahydro-7,8-dimethoxy-2-benzoxepin-1-yl)ethyl]-N-[2-(3,4-dimethoxyphenyl)ethyl]amine,
N-[2-(1,3,4,5-tetrahydro-7,8-dimethoxy-2-benzoxepin-1-yl)ethyl]-N-[2-(3,4-dimethoxyphenyl)ethyl]amine monohydrochloride monohydrate,
1-[2-(1,3,4,5-tetrahydro-7,8-dimethoxy-2-benzoxepin-1-yl)ethyl]-4-(4-chlorophenyl)piperazine,
1-[2-(1,3,4,5-tetrahydro-7,8-dimethoxy-2-benzoxepin-1-yl)ethyl]-4-(2-methoxyphenyl)piperazine,
1-[2-[(1,3,4,5-tetrahydro-7,8-dimethoxy-2-benzoxepin-1-yl)]ethyl]-4-(2,3-dihydro-2-oxo-1H-benzimidazole-1-yl)-piperidine,
1-[2-[(1,3,4,5-tetrahydro-7,8-dimethoxy-2-benzoxepin-1-yl)]ethyl]-4-(2-pyridyl)piperazine,
4-(4-chlorophenyl)-1,2,3,6-tetrahydro-1-[2-(1,3,4,5-tetrahydro-7,8-dimethoxy-2-benzoxepin-1-yl)ethyl]pyridine.

97. A composition according to claim 92 wherein $(R_1)_a$ is 7,8-dimethoxy, $R_2$–$R_3$ and $R_6$–$R_7$ are hydrogen, $R_4$–$R_5$ are methyl and n is one.

98. A composition according to claim 97 wherein the therapeutically effective compound is selected from the group consisting of:
1-[(1,3,4,5-tetrahydro-7,8-dimethoxy-4,4-dimethyl-2-benzoxepin-1-yl)methyl]piperidine,
1-[(1,3,4,5-tetrahydro-7,8-dimethoxy-4,4-dimethyl-2-benzoxepin-1-yl)methyl]piperidine monohydrochloride,
4-methyl-1-[(1,3,4,5-tetrahydro-7,8-dimethoxy-4,4-dimethyl-2-benzoxepin-1-yl)methyl]piperazine,
4-methyl-1-[(1,3,4,5-tetrahydro-7,8-dimethoxy-4,4-dimethyl-2-benzoxepin-1-yl)methyl]piperazine dihydrochloride,
1-[N-(1-n-butyl)amino]methyl-1,3,4,5-tetrahydro-7,8-dimethoxy-4,4-dimethyl-2-benzoxepin,
1-[(1,3,4,5-tetrahydro-7,8-dimethoxy-4,4-dimethyl-2-benzoxepin-1-yl)methyl]morpholine,
1-(N,N-diethylamino)methyl-1,3,4,5-tetrahydro-7,8-dimethoxy-4,4-dimethyl-2-benzoxepin,
1-(1-adamantylamino)methyl-1,3,4,5-tetrahydro-7,8-dimethoxy-4,4-dimethyl-2-benzoxepin.

99. A composition according to claim 92 wherein $(R_1)_a$ is 7,8-dimethoxy, $R_2$–$R_3$ and $R_6$–$R_7$ are hydrogen, $R_4$–$R_5$ are methyl and n is two.

100. A composition according to claim 99 wherein the therapeutically effective compound is selected from the group consisting of:
4-(4-fluorophenyl)-1-[2-(1,3,4,5-tetrahydro-7,8-dimethoxy-4,4-dimethyl-2-benzoxepin-1-yl)ethyl]piperazine,
4-(4-fluorophenyl)-1-[2-(1,3,4,5-tetrahydro-7,8-dimethoxy-4,4-dimethyl-2-benzoxepin-1-yl)ethyl]piperazine dihydrochloride, 4-(3-chlorophenyl)-1-[2-(1,3,4,5-tetrahydro-7,8-dimethoxy-4,4-dimethyl-2-benzoxepin-1-yl)ethyl]piperazine, 4-(3-chlorophenyl)-1-[2-(1,3,4,5-tetrahydro-7,8-dimethoxy-4,4-dimethyl-2-benzoxepin-1-yl)ethyl]piperazine dihydrochloride, 4-(2-chlorophenyl)-1-[2-(1,3,4,5-tetrahydro-7,8-dimethoxy-4,4-dimethyl-2-benzoxepin-1-yl)ethyl]piperazine, 4-(2-chlorophenyl)-1-[2-(1,3,4,5-tetrahydro-7,8-dimethoxy-4,4-dimethyl-2-benzoxepin-1-yl)ethyl]piperazine monohydrochloride, 4-(2-methoxyphenyl)-1-[2-(1,3,4,5-tetrahydro-7,8-dimethoxy-4,4-dimethyl-2-benzoxepin-1-yl)ethyl]piperazine, 4-(2-methoxyphenyl)-1-[2-(1,3,4,5-tetrahydro-7,8-dimethoxy-4,4-dimethyl-2-benzoxepin-1-yl)ethyl]piperazine dihydrochloride monohydrate, 4-(2-methylphenyl)-1-[2-(1,3,4,5-tetrahydro-7,8-dimethoxy-4,4-dimethyl-2-benzoxepin-1-yl)ethyl]piperazine, 4-(2-methylphenyl)-1-[2-(1,3,4,5-tetrahydro-7,8-dimethoxy-4,4-dimethyl-2-benzoxepin-1-yl)ethyl]piperazine dihydrochloride, 4-phenyl-1-[2-(1,3,4,5-tetrahydro-7,8-dimethoxy-4,4-dimethyl-2-benzoxepin-1-yl)ethyl]piperidine, 4-phenyl-1-[2-(1,3,4,5-tetrahydro-7,8-dimethoxy-4,4-dimethyl-2-benzoxepin-1-yl)ethyl]piperidine dihydrochloride, 4-(4-chlorophenyl)-1-[2-(1,3,4,5-tetrahydro-7,8-dimethoxy-4,4-dimethyl-2-benzoxepin-1-yl)ethyl]piperazine, 4-(4-chlorophenyl)-1-[2-(1,3,4,5-tetrahydro-7,8-dimethoxy-4,4-dimethyl-2-benzoxepin-1-yl)ethyl]piperazine dihydrochloride.

101. Compositions of claim 89 wherein W is oxygen and A is selected from the group consisting of —(CH$_2$)$_m$(OCH$_2$CH$_2$)$_q$NR$_{21}$R$_{22}$.

102. Compositions of claim 101 wherein R$_2$ through R$_7$ are the same or different and are selected from the group consisting of hydrogen, alkyl of one to three carbon atoms, inclusive, and cycloalkyl of four through seven carbon atoms, inclusive, when R$_2$ and R$_4$ are taken together with the carbon atom to which they are attached.

103. A composition according to claim 102 wherein (R$_1$)$_a$ is 7,8-dimethoxy, R$_2$–R$_7$ are hydrogen and A is —CH$_2$OCH$_2$CH$_2$NR$_{21}$R$_{22}$.

104. A composition according to claim 103 wherein the therapeutically effective compound is selected from the group consisting of:

1-[2-[(1,3,4,5-tetrahydro-7,8-dimethoxy-2-benzoxepin-1-yl)methoxy]ethyl]-4-[3-(trifluoromethyl)-phenyl]-4-piperidinol, 1-[2-[(1,3,4,5-tetrahydro-7,8-dimethoxy-2-benzoxepin-1-yl)methoxy]ethyl]-4-[3-(trifluoromethyl)-phenyl]-4-piperidinol monochloride hemihydrate, 1-(2-methoxyphenyl)-4-[2-[(1,3,4,5-tetrahydro-7,8-dimethoxy-2-benzoxepin-1-yl)methoxy]ethyl]piperazine, 1-(2-methoxyphenyl)-4-[2-[(1,3,4,5-tetrahydro-7,8-dimethoxy-2-benzoxepin-1-yl)methoxy]ethyl]piperazine dihydrochloride monohydrate, 1-(2-pyridyl)-4-[2-[(1,3,4,5-tetrahydro-7,8-dimethoxy-2-benzoxepin-1-yl)methoxy]ethyl]piperazine, 1-(2-pyridyl)-4-[2-[(1,3,4,5-tetrahydro-7,8-dimethoxy-2-benzoxepin-1-yl)methoxy]ethyl]piperazine hydrochloride, 1-(4-fluorophenyl)-4-[2-[(1,3,4,5-tetrahydro-7,8-dimethoxy-2-benzoxepin-1-yl)methoxy]ethyl]piperazine, 1-(4-fluorophenyl)-4-[2-[(1,3,4,5-tetrahydro-7,8-dimethoxy-2-benzoxepin-1-yl)methoxy]ethyl]piperazine dihydrochloride, 1-[2-[(1,3,4,5-tetrahydro-7,8-dimethoxy-2-benzoxepin-1-yl)methoxy]ethyl]-4-methylpiperazine, 1-[2-[(1,3,4,5-tetrahydro-7,8-dimethoxy-2-benzoxepin-1-yl)methoxy]ethyl]-4-methylpiperazine dihydrochloride dihydrate, 2-[2-[(1,3,4,5-tetrahydro-7,8-dimethoxy-2-benzoxepin-1-yl)methoxy]ethyl]aminoethanol, 2-[2-[(1,3,4,5-tetrahydro-7,8-dimethoxy-2-benzoxepin-1-yl)methoxy]ethyl]aminoethanol cyclohexylsulfamate.

105. A method of treating hypertension in mammals which comprises administering systemically to mammals an effective dose of compounds wherein the compound administered is selected from the group consisting of compounds having the formula:

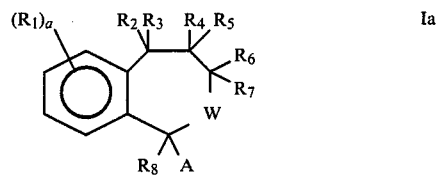

wherein

R$_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one R$_1$ is hydroxy, alkoxy or o-methylenedioxy;

a is one through three;

R$_2$ through R$_7$ are the same or different and are selected from the group consisting of hydrogen, alkyl of one through three carbons, inclusive, hydroxy, alkoxy of one through three carbons; phenyl; halo; cycloalkyl of three through six carbons when R$_2$ and R$_3$, R$_4$ and R$_5$, or R$_6$ and R$_7$ are taken together with the carbon to which they are attached; cycloalkyl of four through seven carbons when R$_2$ and R$_4$ or R$_4$ and R$_6$ are taken together with the carbons to which they are attached; and cycloalkyl of five or six carbons, with the overall provisos that no more than one ring may be attached to any one carbon and that at least two of R$_2$ through R$_7$ are hydrogen, R$_8$ is alkyl of one through three carbons, hydrogen, or phenyl unsubstituted or substituted with a maximum of three substituents selected from the group consisting of alkyl of one through three carbons, halo, alkoxy of one through three carbons, and trihaloalkyl of one to two carbons;

W is oxygen;

and A is selected from the group consisting of:

(i) —(CH$_2$)$_n$NR$_{21}$R$_{22}$, wherein n is one to five and NR$_{21}$R$_{22}$ is selected from the group consisting of NR'$_{21}$R'$_{22}$ wherein R'$_{21}$ and R'$_{22}$ can be the same or different and are selected from the group consisting of H, alkyl of one through four carbons, and together with N to which they are attached form heterocyclic rings of four to six ring atoms; morpholino and $NR_9R_{10}$;

(ii) —$(CH_2)_m$—$(OCH_2CH_2)_q$—$NR_{21}R_{22}$, wherein m and q are each one to three, and $NR_{21}R_{22}$ is selected from the group consisting of $NR''_{21}R''_{22}$ wherein $R''_{21}$ and $R''_{22}$ can be the same or different and are selected from the group consisting of H, alkyl of one through four carbons, and together with the N to which they are attached form heterocyclic rings of four to six ring atoms; morpholino; $NHCH_2CH_2OH$ and $NR_9R_{10}$;

(iii) 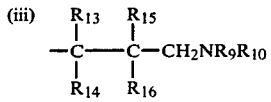

(iv) 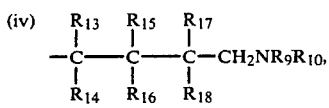

(v) 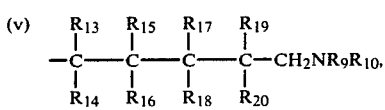

wherein $NR_9R_{10}$ is an amine selected from the group consisting of:

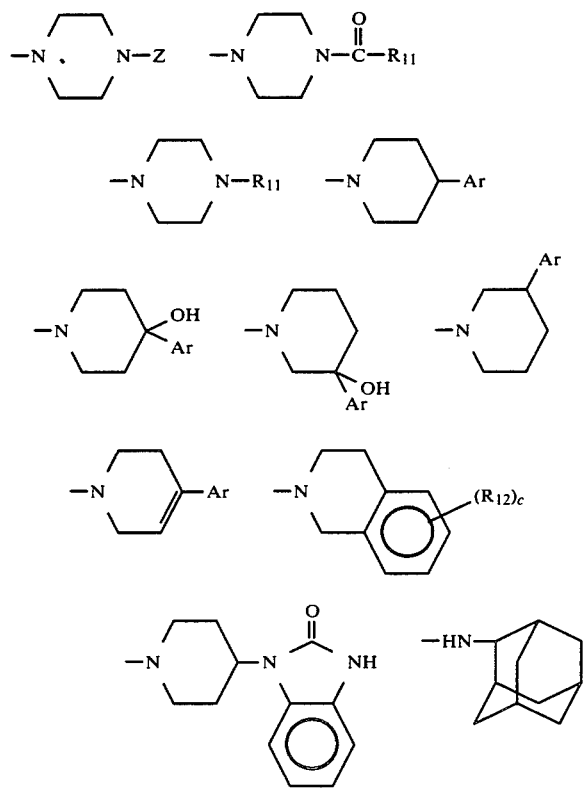

and
—$NHCH_2CH_2Ar'$
wherein $R_{11}$ is alkyl of one through four carbons, 2-furyl, Ar, alkoxy of one to three carbon atoms, inclusive, Z is selected from the group consisting of pyridyl, pyrimidinyl, triazinyl, pyrazinyl, pyridazinyl, pyrrolyl, imidazolyl, pyrazolyl, furyl, tetrazyl, oxazolyl, quinoxalinyl, and quinazolinyl, wherein each member of the group can be unsubstituted or substituted with one or two substituents selected from the group consisting of alkyl of one through three carbons, inclusive, alkoxy of one through three carbons, inclusive, hydroxy, halo, and haloalkyl of one through three carbons, inclusive; provided that Z is not 2-furyl;

$R_{12}$ is alkyl or alkoxy of one through three carbons, hydroxy, halo, or trihalomethyl, $R_{13}$ through $R_{20}$ may be the same or different and are selected from the group hydrogen and alkyl of from 1 to 2 carbon atoms, inclusive; at least one of $R_{13}$ through $R_{20}$ when present being alkyl;

c is zero through two;

Ar and Ar' are phenyl unsubstituted or substituted with one through three substituents selected from the group consisting of alkyl or alkoxy of one through three carbons, hydroxy, halo, and trihaloalkyl or trihaloalkoxy of one or two carbons and pharmaceutically acceptable acid addition salts thereof.

106. A method according to claim 105 wherein a is two or three.

107. A method according to claim 106 when A is the group —$(CH_2)_nNR_9R_{10}$.

108. A method according to claim 107 wherein W is oxygen, $R_2$ through $R_7$ are the same or different and are selected from the group consisting of hydrogen, alkyl of one through three carbon atoms, inclusive and cycloalkyl of four through seven carbon atoms, inclusive, when $R_2$ and $R_4$ or $R_4$ and $R_6$ are taken together with the carbon atom to which they are attached.

109. A method according to claim 108 wherein $R_2$ through $R_7$ are the same or different and are selected from the group consisting of hydrogen, alkyl of one to three carbon atoms, inclusive, and cycloalkyl of four through seven carbon atoms, inclusive, when $R_2$ and $R_4$ are taken together with the carbon atom to which they are attached.

110. A method according to claim 105 wherein W is oxygen and A is the group —$(CH_2)_m$—$(OCH_2CH_2)_qNR_9R_{10}$.

111. A method of treating depression in humans which comprises administering systemically to humans an effective dose of compounds wherein the compound administered is selected from the group consisting of compounds having the formula:

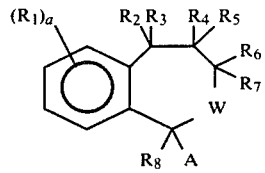

Ia wherein
$R_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one $R_1$ is hydroxy, alkoxy or o-methylenedioxy;

a is one through three;

$R_2$ through $R_7$ are the same or different and are selected from the group consisting of hydrogen, alkyl of one through three carbons, inclusive, hydroxy, alkoxy of one through three carbons; phenyl; halo; cycloalkyl of three through six carbons when $R_2$ and $R_3$, $R_4$ and $R_5$, or $R_6$ and $R_7$ are taken together with the carbon to which they are attached; cycloalkyl of four through seven carbons when $R_2$ and $R_4$ and $R_6$ are taken together with the carbons to which they are attached; and cycloalkyl of five or six carbons, with the overall provisos that no more than one ring may be attached to any one carbon and that at least two of $R_2$ through $R_7$ are hydrogen.

$R_8$ is alkyl of one through three carbons, hydrogen, or phenyl unsubstituted or substituted with a maximum of three substituents selected from the group consisting of alkyl of one through three carbons, halo, alkoxy of one through three carbons, and trihaloalkyl of one to two carbons;

W is oxygen;

and A is selected from the group consisting of (i) —(CH$_2$)$_n$NR$_{21}$R$_{22}$, wherein n is one to five and NR$_{21}$R$_{22}$ is selected from the group consisting of NR'$_{21}$R'$_{22}$ wherein R'$_{21}$ and R'$_{22}$ can be the same or different and are selected from the group consisting of H, alkyl of one through four carbons, and together with N to which they are attached form heterocyclic rings or four to six ring atoms; morpholino and NR$_9$R$_{10}$;

(ii) —(CH$_2$)$_m$—(OCH$_2$CH$_2$)$_q$—NR$_{21}$R$_{22}$, wherein m and q are each one to three, and NR$_{21}$R$_{22}$ is selected from the group consisting of NR''$_{21}$R''$_{22}$ wherein R''$_{21}$ and R''$_{22}$ can be the same or different and are selected from the group consisting of H, alkyl of one through four carbons, and together with the N to which they are attached form heterocyclic rings of four to six ring atoms; morpholino; NHCH$_2$CH$_2$OH and NR$_9$R$_{10}$;

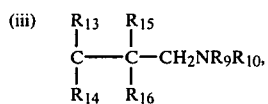

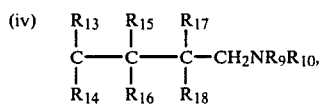

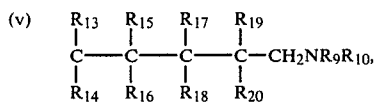

wherein NR$_9$R$_{10}$ is an amine selected from the group consisting of:

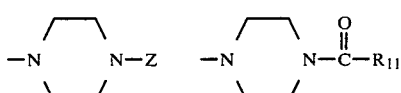

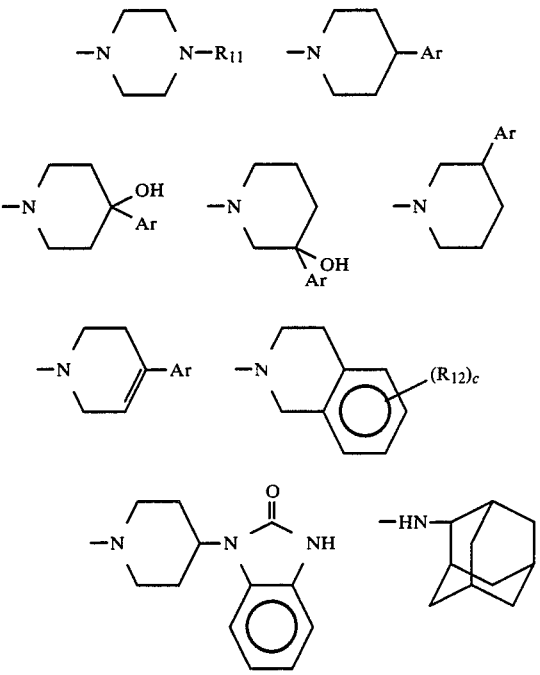

and
—NHCH$_2$CH$_2$Ar' wherein $R_{11}$ is alkyl of one through four carbons, 2-furyl, Ar, alkoxy of one to three carbon atoms, inclusive, Z is selected from the group consisting of pyridyl, pyrimidinyl, triazinyl, pyrazinyl, pyridazinyl, pyrrolyl, imidazolyl, pyrazolyl, furyl, tetrazyl, oxazolyl, quinoxalinyl, and quinazolinyl, wherein each member of the group can be unsubstituted or substituted with one or two substituents selected from the group consisting of alkyl of one through three carbons, inclusive, alkoxy of one through three carbons, inclusive, hydroxy, halo, and haloalkyl of one through three carbons, inclusive; provided that Z is not 2-furyl $R_{12}$ is alkyl or alkoxy of one through three carbons, hydroxy, halo, or trihalomethyl, $R_{13}$ through $R_{20}$ may be the same or different and are selected from the group hydrogen and alkyl of from 1 to 2 carbon atoms, inclusive; at least one of $R_{13}$ through $R_{20}$ when present being alkyl;

c is zero through two;

Ar and Ar' are phenyl unsubstituted or substituted with one through three substituents selected from the group consisting of alkyl or alkoxy of one through three carbons, hydroxy, halo, and trihaloalkyl or trihaloalkoxy of one or two carbons and pharmaceutically acceptable acid addition salts thereof.

112. A method according to claim 111 wherein a is two or three.

113. A method according to claim 112 wherein A is the group —(CH$_2$)$_n$NR$_9$R$_{10}$.

114. A method according to claim 113 wherein W is oxygen, $R_2$ through $R_7$ are the same or different and are selected from the group consisting of hydrogen, alkyl of one through three carbon atoms, inclusive and cycloalkyl of four through seven carbons, inclusive, when R$_2$ and R$_4$ or R$_4$ and R$_6$ are taken together with the carbon atom to which they are attached.

115. A method according to claim 114 wherein R$_2$ through R$_7$ are the same or different and are selected from the group consisting of hydrogen, alkyl of one to three carbon atoms, inclusive, and cycloalkyl of four through seven carbon atoms, inclusive, when R$_2$ and R$_4$ are taken together with the carbon atom to which they are attached.

116. A method according to claim 112 wherein W is oxygen and A is the group —(CH$_2$)$_m$—(OCH$_2$CH$_2$)$_q$NR$_9$R$_{10}$.

117. A method of analgesic treatment in mammals which comprises administering systemically to mammals an effective dose of compounds wherein the compound administered is selected from the group consisting of compounds having the formula:

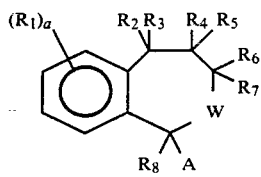

wherein
R$_1$ is the same or different and is selected from the group consisting of alkyl of one through three carbons, inclusive, alkoxy of one through three carbons, inclusive, trihaloalkyl of one or two carbons, hydroxy, halo, trihaloalkoxy of one or two carbons and o-methylenedioxy with the proviso that at least one R$_1$ is hydroxy, alkoxy or o-methylenedioxy;

a is one through three;

R$_2$ through R$_7$ are the same or different and are selected from the group consisting of hydrogen, alkyl of one through three carbons, inclusive, hydroxy, alkoxy of one through three carbons; phenyl; halo; cycloalkyl of three through six carbons when R$_2$ and R$_3$, R$_4$ and R$_5$, or R$_6$ and R$_7$ are taken together with the carbon to which they are attached; cycloalkyl of four through seven carbons when R$_2$ and R$_4$ or R$_4$ and R$_6$ are taken together with the carbons to which they are attached; and cycloalkyl of five or six carbons, with the overall provisos that no more than one ring may be attached to any one carbon and that at least two of R$_2$ through R$_7$ are hydrogen.

R$_8$ is alkyl of one through three carbons, hydrogen, or phenyl unsubstituted or substituted with a maximum of three substituents selected from the group consisting of alkyl of one through three carbons, halo, alkoxy of one through three carbons, and trihaloalkyl of one to two carbons;

W is oxygen;

and A is selected from the group consisting of:
(i) —(CH$_2$)$_n$NR$_{21}$R$_{22}$, wherein n is one to five and NR$_{21}$R$_{22}$ is selected from the group consisting of NR'$_{21}$R'$_{22}$ wherein R'$_{21}$ and R'$_{22}$ can be the same or different and are selected from the group consisting of H, alkyl of one through four carbons, and together with N to which they are attached from heterocyclic rings of four to six ring atoms; morpholino and NR$_9$R$_{10}$;
(ii) —(CH$_2$)$_m$—(OCH$_2$CH$_2$)$_q$—NR$_{21}$R$_{22}$, wherein m and q are each one to three, and NR$_{21}$R$_{22}$ is selected from the group consisting of NR"$_{21}$R"$_{22}$ wherein R"$_{21}$ and R"$_{22}$ can be the same or different and are selected from the group consisting of H, alkyl of one through four carbons, and together with the N to which they are attached form heterocyclic rings of four to six ring atoms; morpholino; NHCH$_2$CH$_2$OH and NR$_9$R$_{10}$;

(iii) 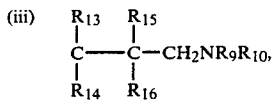

(iv) 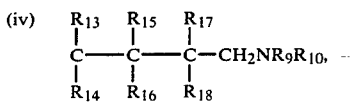

(v) 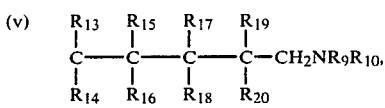

wherein NR$_9$R$_{10}$ is an amine selected from the group consisting of:

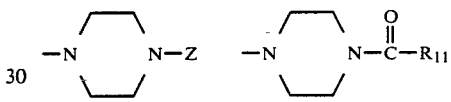

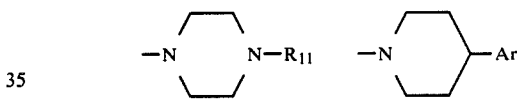

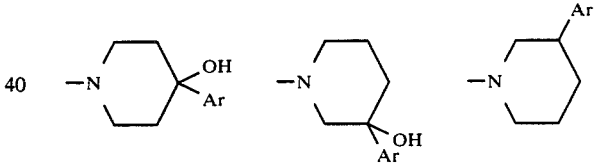

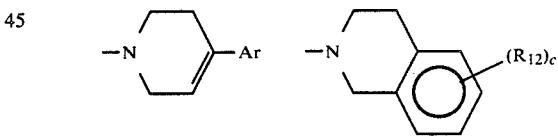

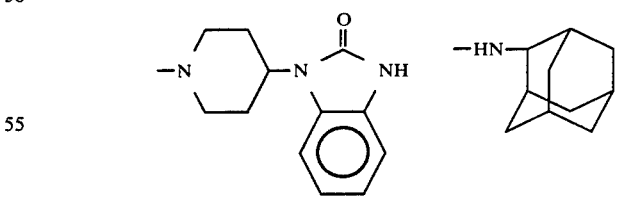

and
—NHCH$_2$CH$_2$Ar' wherein R$_{11}$ is alkyl of one through four carbons, 2-furyl, Ar, alkoxy of one to three carbon atoms, inclusive, Z is selected from the group consisting of pyridyl, pyrimidinyl, triazinyl, pyrazinyl, pyridazinyl, pyrrolyl, imidazolyl, pyrazolyl, furyl, tetrazyl, oxazolyl, quinoxalinyl, and quinazolinyl, wherein each member of the group can be unsubstituted or substituted with one or two substituents selected from the group consisting of alkyl of one through three carbons, inclusive, alkoxy of one through three carbons, inclusive, hydroxy, halo, and haloalkyl of one through three carbons, inclusive; provided that Z is not 2-furyl;

$R_{12}$ is alkyl or alkoxy of one through three carbons, hydroxy, halo, or trihalomethyl, $R_{13}$ through $R_{20}$ may be the same or different and are selected from the group hydrogen and alkyl of from 1 to 2 carbon atoms, inclusive; at least one of $R_{13}$ through $R_{20}$ when present being alkyl;

c is zero through two

Ar and Ar' are phenyl unsubstituted or substituted with one through three substituents selected from the group consisting of alkyl or alkoxy of one through three carbons, hydroxy, halo, and trihaloalkyl or trihaloalkoxy of one or two carbons and pharmaceutically acceptable acid addition salts thereof.

118. A method according to claim 117 wherein a is two or three.

119. A method according to claim 118 wherein A is the group $-(CH_2)_nNR_9R_{10}$.

120. A method according to claim 119 wherein W is oxygen, $R_2$ through $R_7$ are the same or different and are selected from the group consisting of hydrogen, alkyl of one through three carbon atoms, inclusive and cycloalkyl of four through seven carbon atoms, inclusive, when $R_2$ and $R_4$ or $R_4$ and $R_6$ are taken together with the carbon atom to which they are attached.

121. A method according to claim 120 wherein $R_2$ through $R_7$ are the same or different and are selected from the group consisting of hydrogen, alkyl of one to three carbon atoms, inclusive, and cycloalkyl of four through seven carbon atoms, inclusive, when $R_2$ and $R_4$ are taken together with the carbon atom to which they are attached.

122. A method according to claim 118 wherein W is oxygen and A is the group $-(CH_2)_m-(OCH_2CH_2)_qNR_9R_{10}$.

* * * * *